United States Patent [19]
Turner et al.

[11] Patent Number: 5,677,193
[45] Date of Patent: Oct. 14, 1997

[54] METHOD AND APPARATUS FOR PROCESSING A TEST SAMPLE TO CONCENTRATE AN ANALYTE IN THE SAMPLE FROM A SOLVENT IN THE SAMPLE

[75] Inventors: Terry D. Turner; Laurence S. Beller, both of Idaho Falls; Michael L. Clark, Menan; Kerry M. Klingler, Idaho Falls, all of Id.

[73] Assignee: Lockheed Martin Idaho Technologies Company, Idaho Falls, Id.

[21] Appl. No.: 264,409

[22] Filed: Jun. 23, 1994

[51] Int. Cl.[6] .............. G01N 1/18; B01D 51/08; B01D 11/00
[52] U.S. Cl. .......... 436/177; 436/178; 422/189; 422/193; 95/29; 95/277; 203/43; 203/DIG. 2; 202/168; 202/169; 202/185.1
[58] Field of Search .................. 436/178, 177; 95/29; 96/175; 55/277; 203/43, DIG. 2; 202/168, 169, 185.1; 422/189, 193

[56] References Cited

U.S. PATENT DOCUMENTS

| | | | |
|---|---|---|---|
| 440,963 | 11/1890 | Pinagel | 203/DIG. 2 |
| 777,115 | 12/1904 | Lloyd | 203/DIG. 2 |
| 808,997 | 1/1906 | Lloyd | 203/DIG. 2 |
| 2,095,056 | 10/1937 | Clough | 23/259 |
| 2,182,564 | 12/1939 | Leibuff | 167/74 |
| 2,476,477 | 7/1949 | Berg | 257/34 |
| 2,573,807 | 11/1951 | Piros et al. | 202/153 |
| 2,732,415 | 1/1956 | Klinge | 260/705 |

(List continued on next page.)

OTHER PUBLICATIONS

Kontes Environmental Products, Catalogue of May 1988, p. 4.
Supielco Chromatography Supplies, Catalogue 24 of 1986, p. 184.
Kontes, Chemistry and Life Sciences Products, 1989 Catalogue, p. 33.
Catalog: Scientific Apparatus for Environmental Testing & Org Analyses (1989), published by the Burkett Group, Burkett Consultants, Inc.
Knotes Catalog re: Evaporative Concentrators; Vineland, N.J., 1992; pp. 154–155.
Kimble Scientific Products Catalog re: Separatory Funnels; Vineland, N.J., 1991; p. 98.
Ace Glass Catalog re: Distilling Heads; Vineland, N.J., pp. 102–103; re: Reaction Equipment pp. 134–135, 137; re: Mini-Lab Funnels, pp. 364–365.

*Primary Examiner*—Nina Bhat
*Attorney, Agent, or Firm*—Wells St. John Roberts Gregory & Matkin

[57] ABSTRACT

A method of processing a test sample to concentrate an analyte in the sample from a solvent in the sample includes: a) boiling the test sample containing the analyte and solvent in a boiling chamber to a temperature greater than or equal to the solvent boiling temperature and less than the analyte boiling temperature to form a rising sample vapor mixture; b) passing the sample vapor mixture from the boiling chamber to an elongated primary separation tube, the separation tube having internal sidewalls and a longitudinal axis, the longitudinal axis being angled between vertical and horizontal and thus having an upper region and a lower region; c) collecting the physically transported liquid analyte on the internal sidewalls of the separation tube; and d) flowing the collected analyte along the angled internal sidewalls of the separation tube to and pass the separation tube lower region. The invention also includes passing a turbulence inducing wave through a vapor mixture to separate physically transported liquid second material from vaporized first material. Apparatus are also disclosed for effecting separations. Further disclosed is a fluidically powered liquid test sample withdrawal apparatus for withdrawing a liquid test sample from a test sample container and for cleaning the test sample container.

13 Claims, 8 Drawing Sheets

U.S. PATENT DOCUMENTS

| | | | |
|---|---|---|---|
| 3,291,103 | 12/1966 | Dvonch et al. | 202/181 |
| 3,416,999 | 12/1968 | Sheperd et al. | 202/161 |
| 3,527,576 | 9/1970 | Kaplan et al. | 23/229 |
| 3,578,567 | 5/1971 | Malvin et al. | 203/49 |
| 3,803,004 | 4/1974 | Egri | 203/29 |
| 3,960,668 | 6/1976 | Rush | 202/185 |
| 4,006,062 | 2/1977 | Bhucher et al. | 202/169 |
| 4,255,386 | 3/1981 | Schachter et al. | 422/101 |
| 4,337,121 | 6/1982 | English | 202/169 |
| 4,938,785 | 7/1990 | MacPherson, Jr. et al. | 55/1 |
| 5,017,500 | 5/1991 | Langer | 436/178 |
| 5,098,662 | 3/1992 | Killough | 422/102 |
| 5,147,562 | 9/1992 | Heyman | 210/748 |
| 5,176,749 | 1/1993 | Rue et al. | 202/185.3 |
| 5,217,904 | 6/1993 | Bruno | 436/181 |
| 5,236,555 | 8/1993 | Yuan | 202/153 |
| 5,277,707 | 1/1994 | Munk et al. | 95/8 |
| 5,282,927 | 2/1994 | Weidner | 159/147.1 |
| B1 5,098,662 | 4/1994 | Kilough | 422/102 |

FIG. II

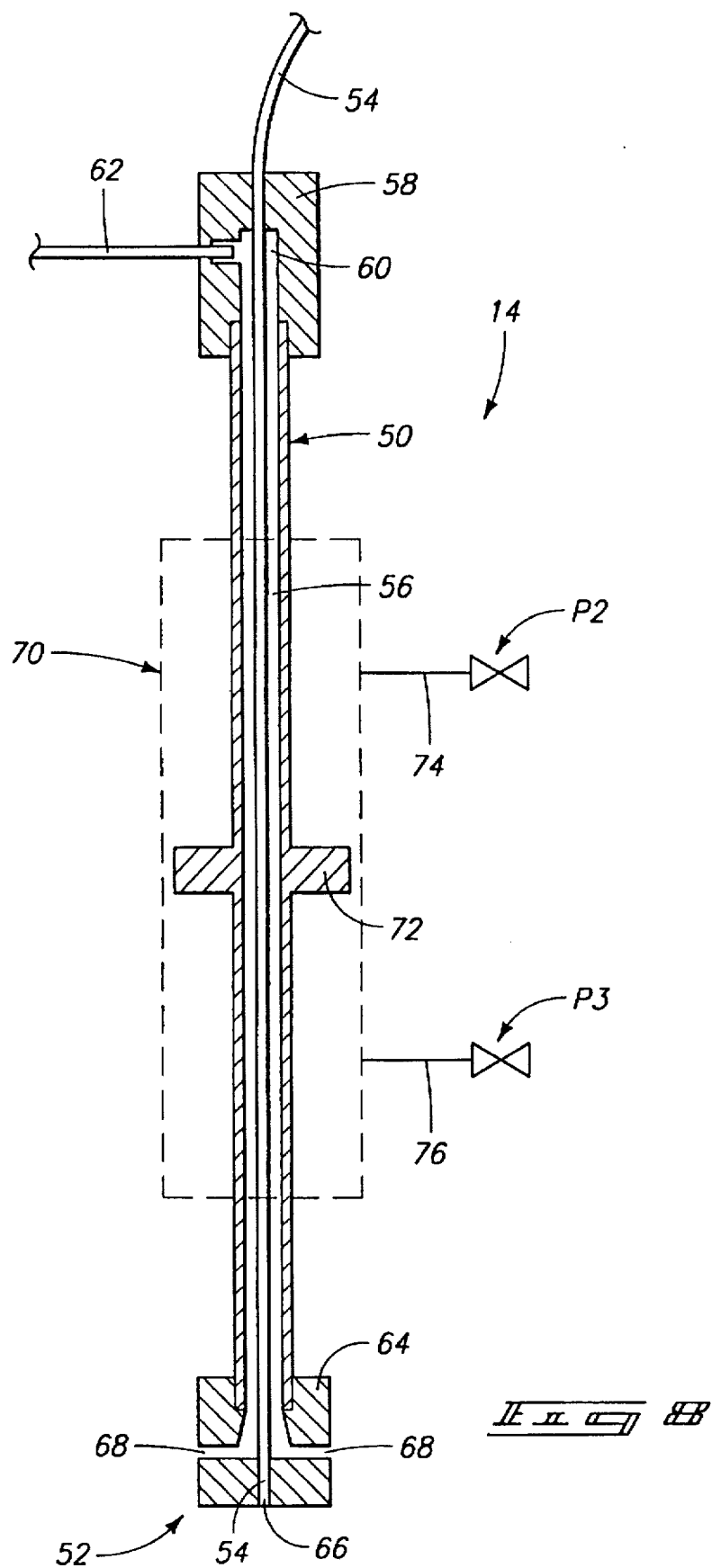

METHOD AND APPARATUS FOR PROCESSING A TEST SAMPLE TO CONCENTRATE AN ANALYTE IN THE SAMPLE FROM A SOLVENT IN THE SAMPLE

CONTRACTUAL ORIGIN OF THE INVENTION

The United States Government has rights in this invention pursuant to Contract No. DE-AC07-76ID01570 between the United States Department of Energy and EG&G Idaho, Inc.

TECHNICAL FIELD

This invention relates to methods of processing test samples to concentrate an analyte in the sample from a solvent in the sample, and to apparatus for conducting such methods. The invention also relates to distillation methods for separating lower boiling point materials from higher boiling point materials in a liquid mixture of such materials.

BACKGROUND OF THE INVENTION

Environmental chemistry includes the analysis of soil samples to qualitatively and quantitatively determine presence of contaminants. Current analytical chemistry procedures are very time consuming and labor intensive, and will not realistically meet future needs generated by the U.S. Department Of Energy's environmental restoration and waste management programs.

Accurate soil sample analysis is a critical determination. Before remediation of problem areas can begin, the type and extent of contamination must be determined. Samples to be analyzed must be retrieved from the site and transported to a facility capable of analytical chemistry. The soil sample is processed to remove constituents that are not of interest and to isolate the contaminating substances. Once the sample has been processed and prepared, it is submitted for spectral analysis to determine content and concentration. Now, a trained scientist is required to determine if the concentration levels indicate contamination or are just indicative of background levels. As a precaution, spiked samples are processed with the actual sample. These spiked samples are used to verify that the process is yielding direct results and all must be analyzed the same way.

The protocol that includes all of the tasks from sample retrieval to output of characterization information has been designated as a standard analysis method, or SAM for short. If SAMs could be automated, laboratory technicians would be able to perform analytical analysis in a fraction of the time and cost of conventional prior art methods.

A SAM typically consists of three categories of operations: sample preparation, analysis, and data interpretation. Imbedded within the different areas of the SAM are many smaller tasks, such as weighing the sample or concentrate. Often these steps are repeated several times during the course of a SAM and are common to several SAMs. In accordance with an aspect of the invention, the equipment required to perform individual steps has been developed into automated modules.

Common to many SAMs are filtration and liquid concentration. This invention principally concerns methods and apparatus for processing a test sample to concentrate an analyte in the sample from a solvent in the sample. Present concentration methods employ what is known as the Snyder column and Kuderna-Danish concentration methods. The Snyder column comprises an elongated vertically oriented column having a series of spaced, non-contacting glass balls retained therealong. The balls of the Snyder column increases reflux, thereby separating analytes from the rising hot solvent vapors. It is theorized that the analytes, which have a higher boiling point than the solvents, are in part being physically transported out on solvent vapors. The reflux created by the Snyder column strips the physically transported analytes from the rising hot vapors, and allows them to return to the boiling chamber.

Typically, this prior art step is reported to take from 60 to 90 minutes. The current concentration procedure is a sensitive and precise operation which requires a skilled technician. The sample is first heated to the boiling point of the solvent, and then concentrated with the Snyder column. The solvent evaporates until the sample is concentrated to between 1 and 2 milliliters.

Although this invention spawned from research associated with development of a standard laboratory module in conducting an overall automated process for analyzing test samples in accordance with EPA standards, those skilled in the art will find other uses of the invention which is intended to be limited only by the accompanying claims appropriately interpreted in accordance with the Doctrine of Equivalents.

BRIEF DESCRIPTION OF THE DRAWINGS

Preferred embodiments of the invention are described below with reference to the following accompanying drawings.

FIG. 8 is a diagrammatic sectional view of a sample withdrawal apparatus in accordance with the invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with an aspect of the invention, a method of processing a test sample to concentrate an analyte in the sample from the solvent in the sample comprises the following steps:

boiling the test sample containing the analyte and solvent in a boiling chamber to a temperature greater than or equal to the solvent boiling temperature and less than the analyte boiling temperature to form a rising sample vapor mixture, the sample vapor mixture comprising vaporized solvent and liquid analyte physically transported therewith;

passing the sample vapor mixture from the boiling chamber to an elongated primary separation tube, the primary separation tube having internal sidewalls and a longitudinal axis, the longitudinal axis being angled between vertical and horizontal and thus having an upper region and a lower region;

collecting the physically transported liquid analyte on the internal sidewalls of the separation tube; and flowing the collected analyte along the angled internal sidewalls of the separation tube to and past the separation tube lower region.

In accordance with another aspect of the invention, a distillation method for separating a lower boiling point first material from a higher boiling point second material in a liquid mixture of such materials comprises the following steps:

boiling the liquid mixture to a temperature greater than or equal to the boiling point of the first material to form a vapor mixture, the vapor mixture comprising vaporized first material and liquid second material physically transported therewith; and passing a turbulence inducing wave through the vapor mixture to separate the physically transported liquid second material from the vaporized first material.

The invention further comprises liquid/vapor separation apparatus which comprises:

a hollow tubular elongated body section having opposing end regions, a longitudinal axis and a longitudinal length;

an inlet passage extending from one of the end regions, the inlet passage being sized and shaped to connect with a liquid/vapor mixture source;

an outlet passage extending from the other end region; and an ultrasonic transducer associated with the elongated body section to induce ultrasonic waves within the elongated body section.

Other aspects and features of the invention will be apparent from the following discussion and concluding claims.

Figure 1:
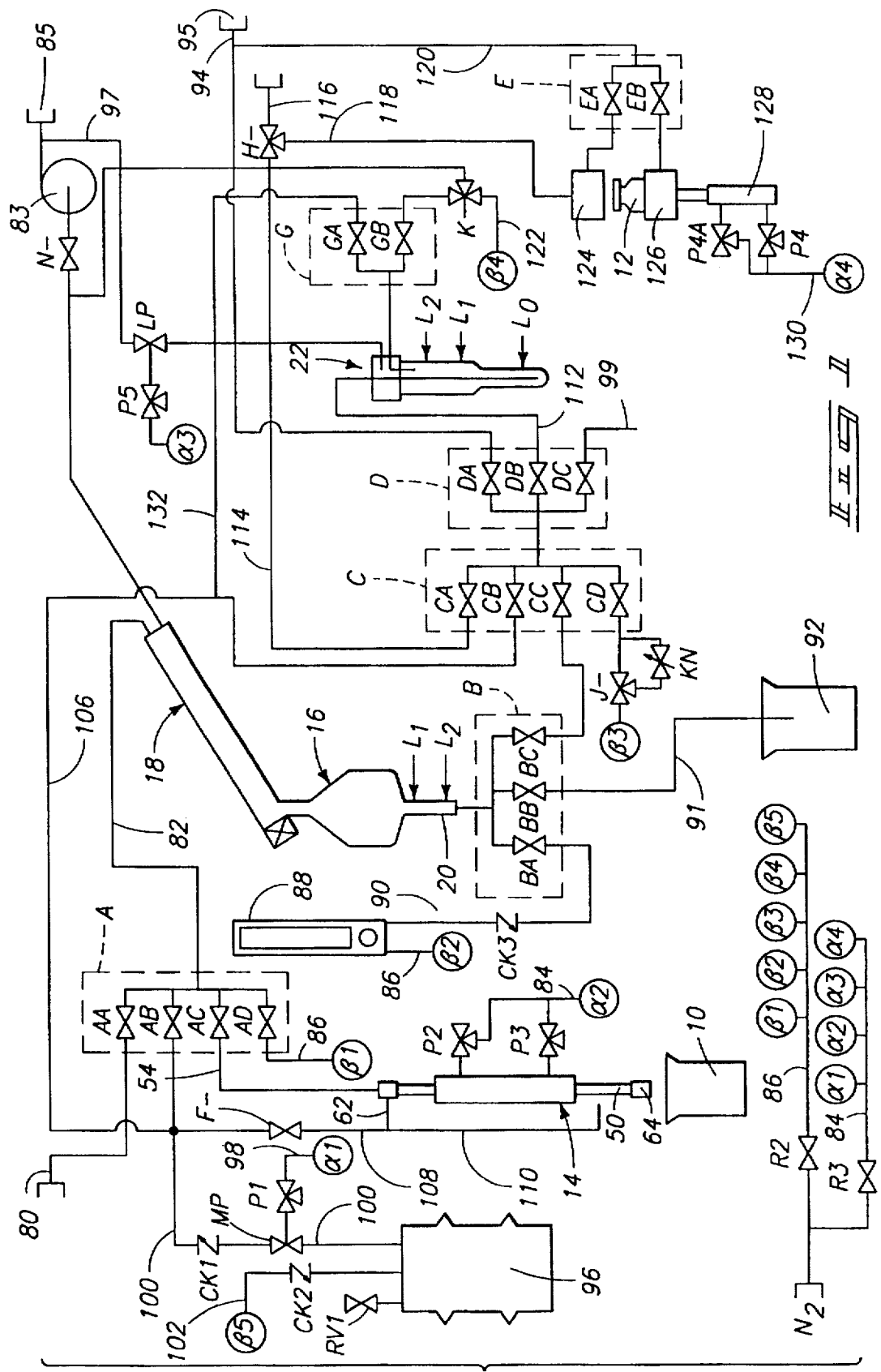
FIG. 1 is a schematic representation of a method in accordance with the invention.

Referring first to FIG. 1, a modular system of processing a test sample to concentrate an analyte in the sample from a solvent in the sample is schematically shown. Such includes an inlet beaker 10 having the sample to be concentrated, and an outlet vial 12 which collects sample concentrated by the module. An extraction device 14 collects liquid sample from beaker 10 and transfers such sample through associated tubing to a boiling chamber 16. There, the lower boiling point solvents are vaporized and undesirably transport a quantity of liquid analyte physically therewith out of boiling chamber 16. The transported analyte is separated from the solvent vapors in an elongated primary separation tube 18, and returned to boiling chamber 16. The lower portion of boiling chamber 16 comprises an elongated tubular portion 20 within which concentrated sample is collected. Concentrated sample from portion 20 is transferred via associated tubing to a container apparatus 22 for further concentration and/or volume adjustment, as desired. Liquid from container apparatus 22 is transferred via associated tubing to outlet vial 12 for transfer out of the instrument.

Figure 2:
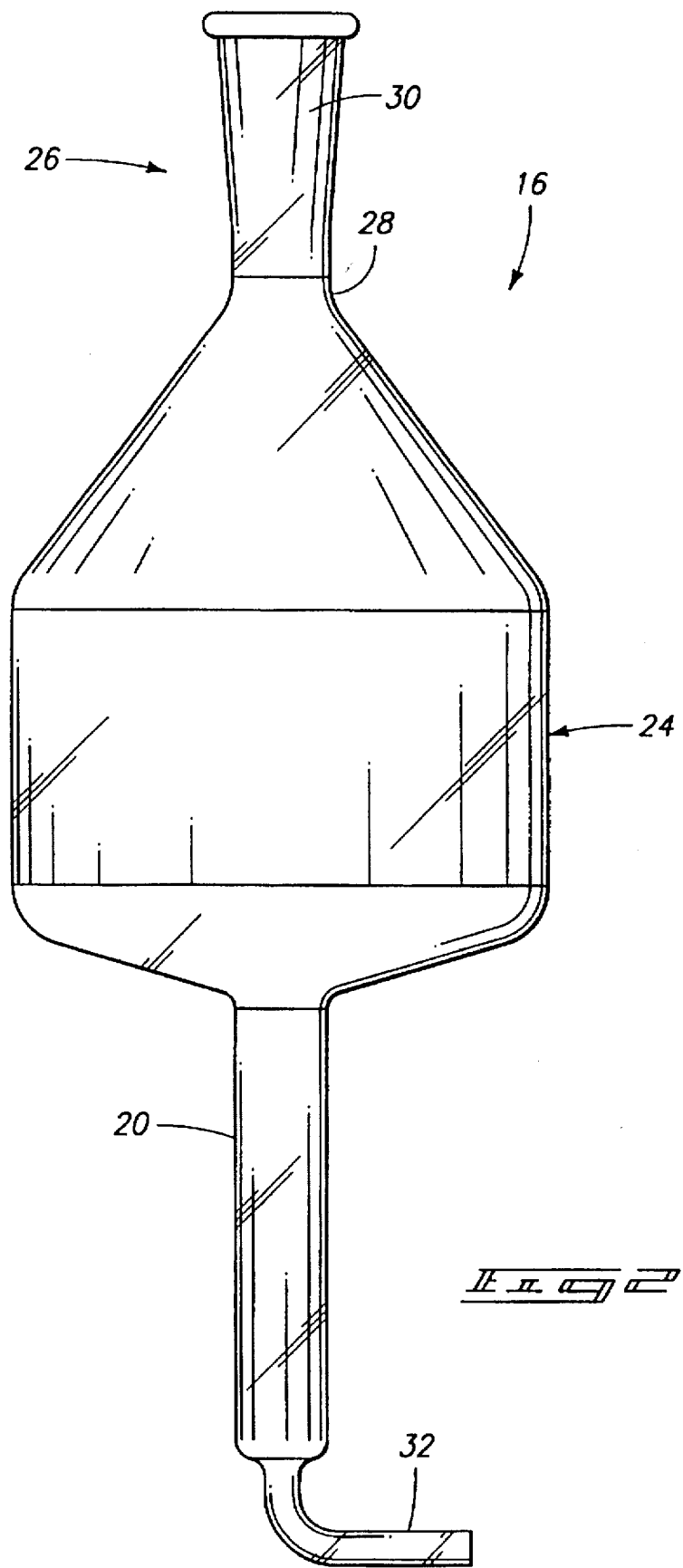
FIG. 2 is an elevational view of a boiling chamber used in the FIG. 1 method.
Figure 3:
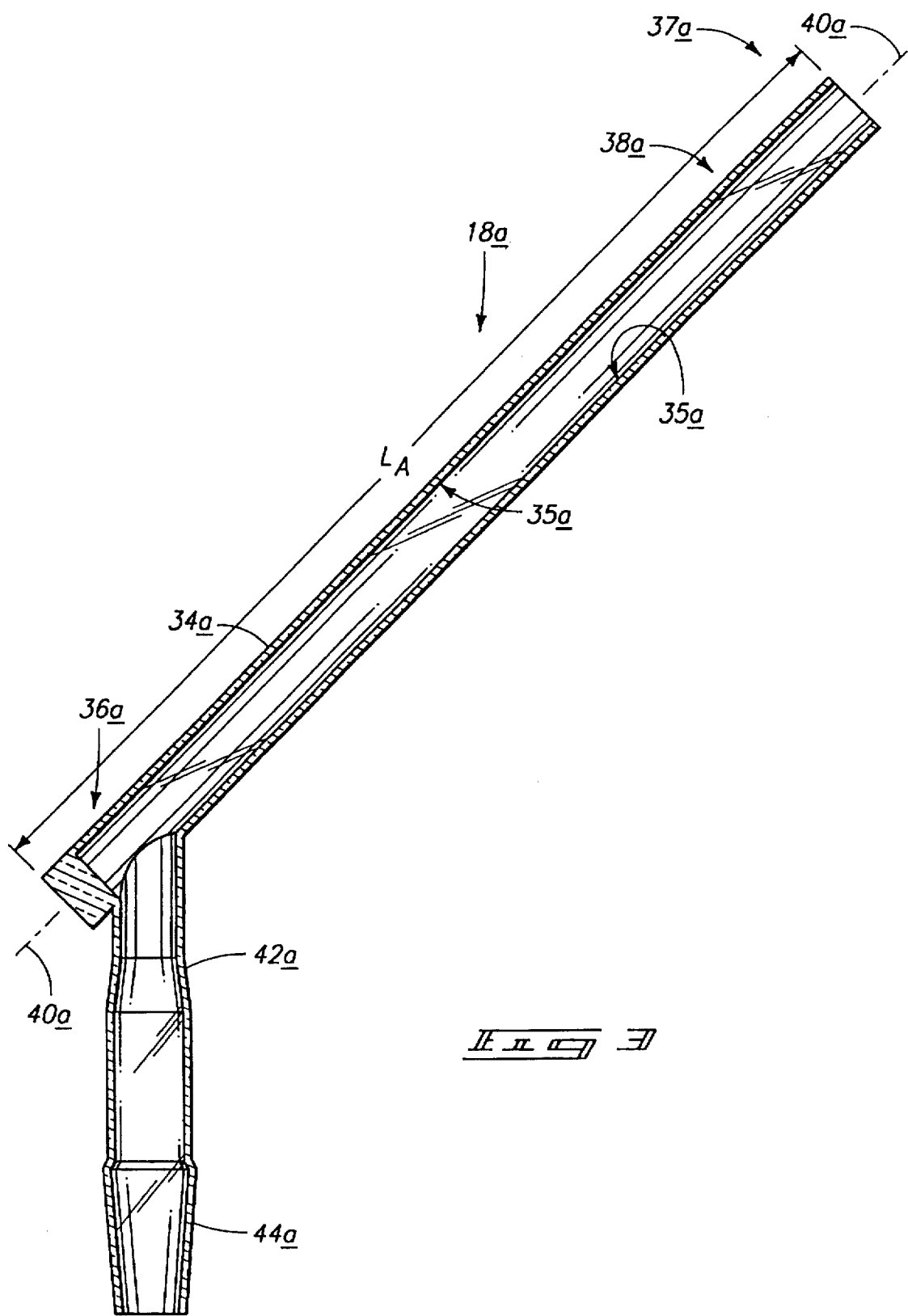
FIG. 3 is a diagrammatic sectional view of a liquid/vapor separation apparatus in accordance with the invention.
Figure 4:
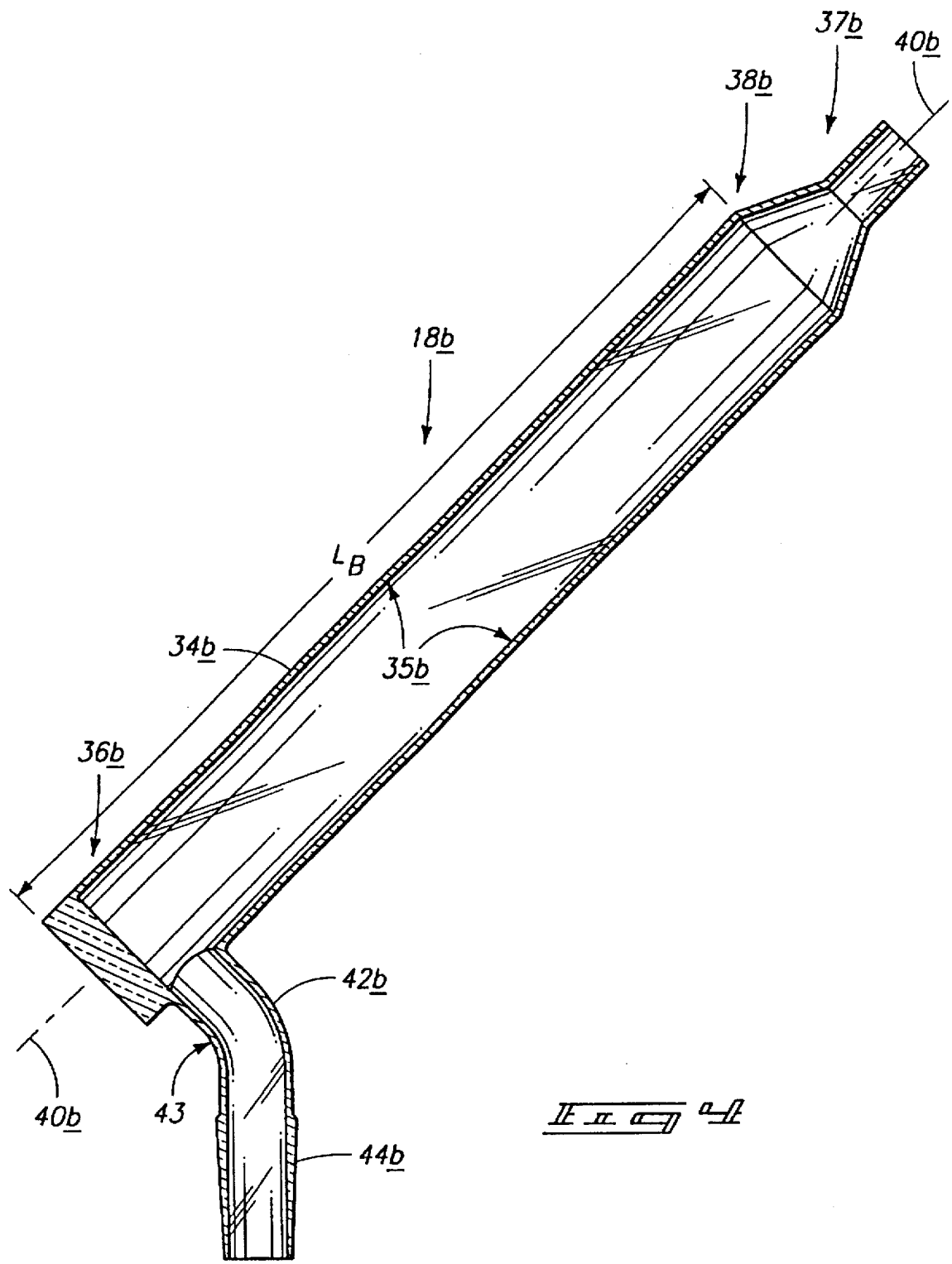
FIG. 4 is an diagrammatic sectional view of an alternate and preferred embodiment liquid/vapor separation apparatus in accordance with the invention.

The discussion proceeds with reference to FIGS. 2–4 for more detailed description of the construction and method of operation of boiling chambers and separation tubes, in accordance with the invention. Referring first to FIG. 2, boiling chamber 16 comprises a central body portion 24, lower concentrated analyte collection tube 20, and upper portion 26. A suitable heating element would be wrapped about central portion 24, and a second heating element wrapped around collection tube 20, for boiling the test sample. An example would be to spray coat each portion with metal and connect respective electrodes thereto. Current applied through the coated metal would generate the desired heat. Preferably if coating collection tube 20 with metal, a vertically oriented slot is provided in the metal to enable optical detection of sample presence within tube 20. Thermocouples would be provided in the side of container 16 for monitoring temperature and corresponding heat input to the boiling sample.

Upper portion 26 of boiling chamber 16 tapers downwardly to a neck 28, and constitutes a mating connector extension 30 for attachment with an elongated separation tube. Example alternate separation tubes 18a, 18b, 18c and 18d are shown in FIGS. 3, 4, 5 and 6/7, respectively. A tubular extension 32 extends from the bottom portion of sample collection tube 20 for transferring concentrated sample away from chamber 16.

Referring more specifically first to FIGS. 3 and 4, liquid/vapor separation apparatus 18a and 18b comprise respective hollow tubular elongated body sections 34a, 34b. Each has opposing end regions 36a, 36b, and 38a, 38b, respectively. Each has an associated longitudinal axis 40a, 40b, respectively, and a longitudinal length $L_A$ and $L_B$, respectively. Each also includes respective internal sidewalls 35a and 35b which are straight along their respective longitudinal length $L_A$ and $L_B$.

Inlet passages 42a and 42b extend from end regions 36a and 36b, respectively. Passages 42a and 42b includes respective male connections 44a and 44b sized and shaped for mating fluid communication connection with connector region 30 of boiling chamber 16. Thus, the respective inlet passages 42a, 42b are sized and shaped to connect with an external liquid/vapor mixture source, such as boiling chamber 16 through its associated connector region 30. Passageway 42a engages with tubular body 34a at an angle of approximately 45° relative to longitudinal axis 40a. Inlet passage 42a extends straight downwardly from the connection point with tubular body 34a. Passage 42b engages with tubular body 34b at a 90° angle relative to longitudinal axis 40b, but bends at location 43 such that longitudinal axis 40b is angled at approximately 45° relative to the mating connection of connector 44b. Thus, inlet passage 42b is other than straight due to bend 43. Further, each inlet passage 42a, 42b is effectively angled at other than 90° and at other than 180° relative to the respective longitudinal elongated body axes 40a and 40b. In the context of this document, a 180° connection would refer to joining with the separation tube along the longitudinal axis such that the tube would connect and extend vertically relative to the orientation of boiling chamber 16.

Outlet passage regions 37a and 37b extend from end regions 38a and 38b, respectively. Outlet passage 37b illustrates a preferred tapered connection, while outlet passage 35a illustrates a straight-wall outlet.

A method of processing a test sample to concentrate an analyte in the sample from a solvent in the sample using boiling chamber 16 and either of liquid/vapor separation apparatus 18a or 18b can now be described. The discussion proceeds with respect to the separate apparatus of FIGS. 3 and 4 without use of the "a" and "b" suffixes where the differing details in construction of such apparatus are not particularly pertinent to this part of the discussion. Initially, separation tube 18 is mated with boiling chamber 16 via male and female connections 44, 30, respectively. Thus, lower or inlet region 36 of separation tube 18 is elevationally higher than boiling chamber 16, and connected therewith. Test sample containing the analyte and solvent are brought to a boil within boiling chamber 16 to a temperature greater than or equal to the solvent boiling temperature and less than the analyte boiling temperature, thus forming a rising sample vapor mixture. Vacuum pressure in the boiling chamber is preferably used to reduce the boiling temperature of the solvent. The sample vapor mixture comprises vaporized solvent and liquid analyte physically transported therewith. The sample vapor mixture is passed from boiling chamber 16 to elongated separation tube 34 via passageway 42, with passageway 42a being straight and passageway 42b being other than straight. Longitudinal axis 40 is angled between vertical and horizontal relative to the sample vapor mixture vertically rising from boiling chamber 16.

Liquid analyte physically transported with the solvent vapor collects on internal sidewalls 39 of elongated separation tube 34, thus further separating analyte and vapor. The wall temperature of separation tube 34 is preferably maintained below the boiling point of the solvent, thus condensing the solvent vapors that come into contact with the internal sidewall and preventing re-vaporization. The collected or separated analyte and any liquid solvent flows along angled internal sidewalls 35 to separation tube 34 to and past separation tube lower region 36. Passageway 42 is preferably void of horizontal sections to facilitate gravity flow of collected analyte from separation tube 34b back into boiling chamber 16.

Advantages over the Kuderna-Danish apparatus separation method including the Snyder column will be apparent. The Snyder column is difficult to clean because of the plurality of hard-to-reach separation balls, which can be eliminated in the above-described apparatus. It has been determined that the angled nature of the internal sidewalls 35 significantly facilitates and enables analyte/solvent separation beyond use of a straight vertically oriented column alone. One example preferred liquid/vapor separation apparatus is that shown by FIG. 4. Such includes a tubular portion 34b which, with use of ultrasonics as described below, is sized to correspond to the ultrasonic wave frequency. Further, bending of passageway 42b at 43 is believed to facilitate greater exposure of the rising sample vapor mixture to sidewall area to facilitate separation. Additionally, the inwardly tapered outlet region 35b likewise facilitates and requires greater sidewall exposure of the physically transported analyte.

Liquid/vapor separation in accordance with the above and another aspect of the invention further comprises passing a turbulence-inducing wave through the vapor mixture having the physically transported higher boiling point material to separate such material from the vaporized first material. Such preferably occurs in a chamber other than the boiling chamber, such as in a separate separation chamber 18. Example turbulence-inducing waves include acoustic waves, such as sonic waves and more particularly ultrasonic waves. Alternately and by way of example only, such turbulence-inducing wave could comprise pulsing vacuum pressure or alternately a pressurized gas through the vapor mixture.

Figure 5:
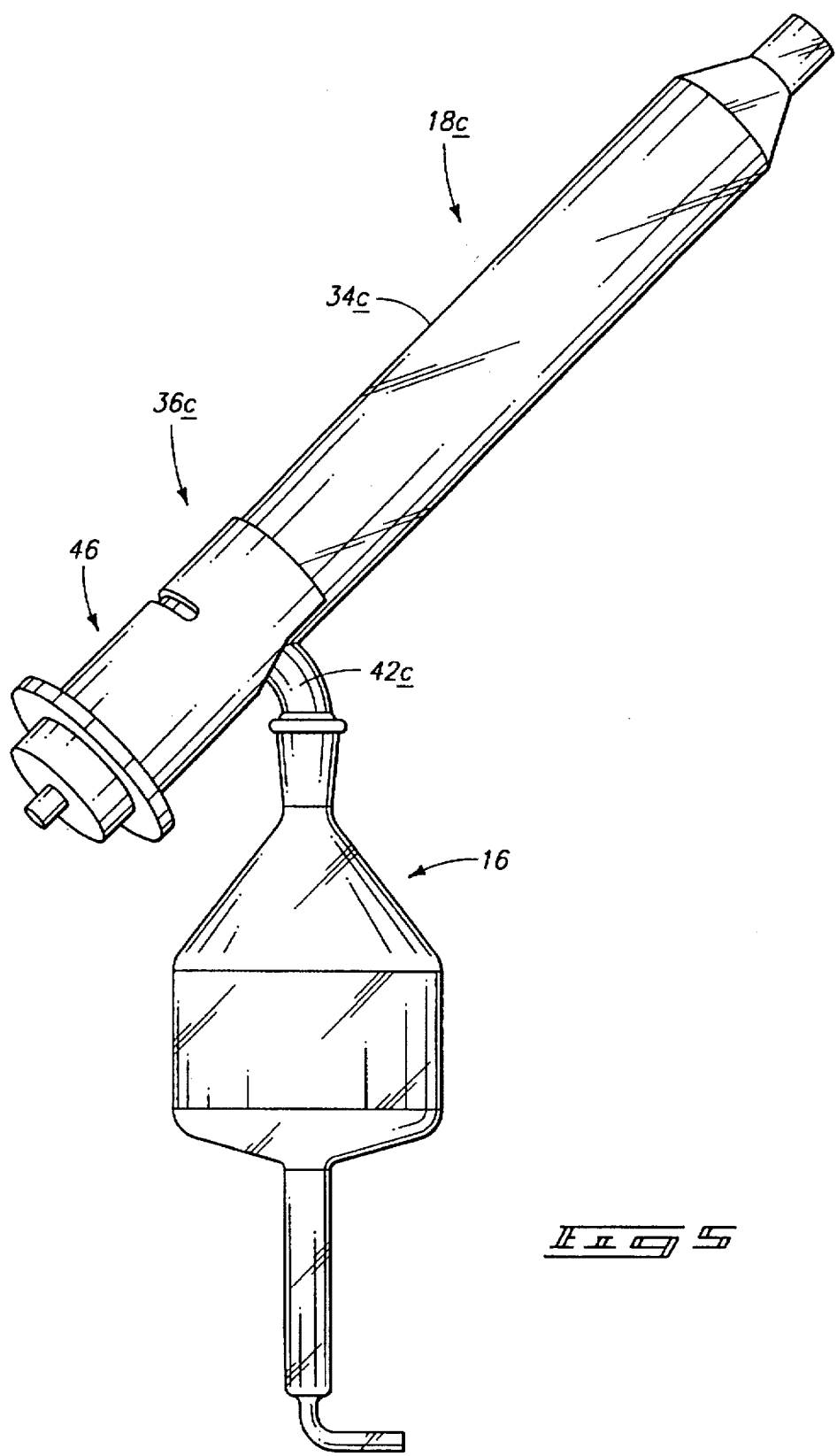
FIG. 5 is an elevational view of a boiling chamber and liquid/vapor separation apparatus in accordance with the invention.
Figure 6:
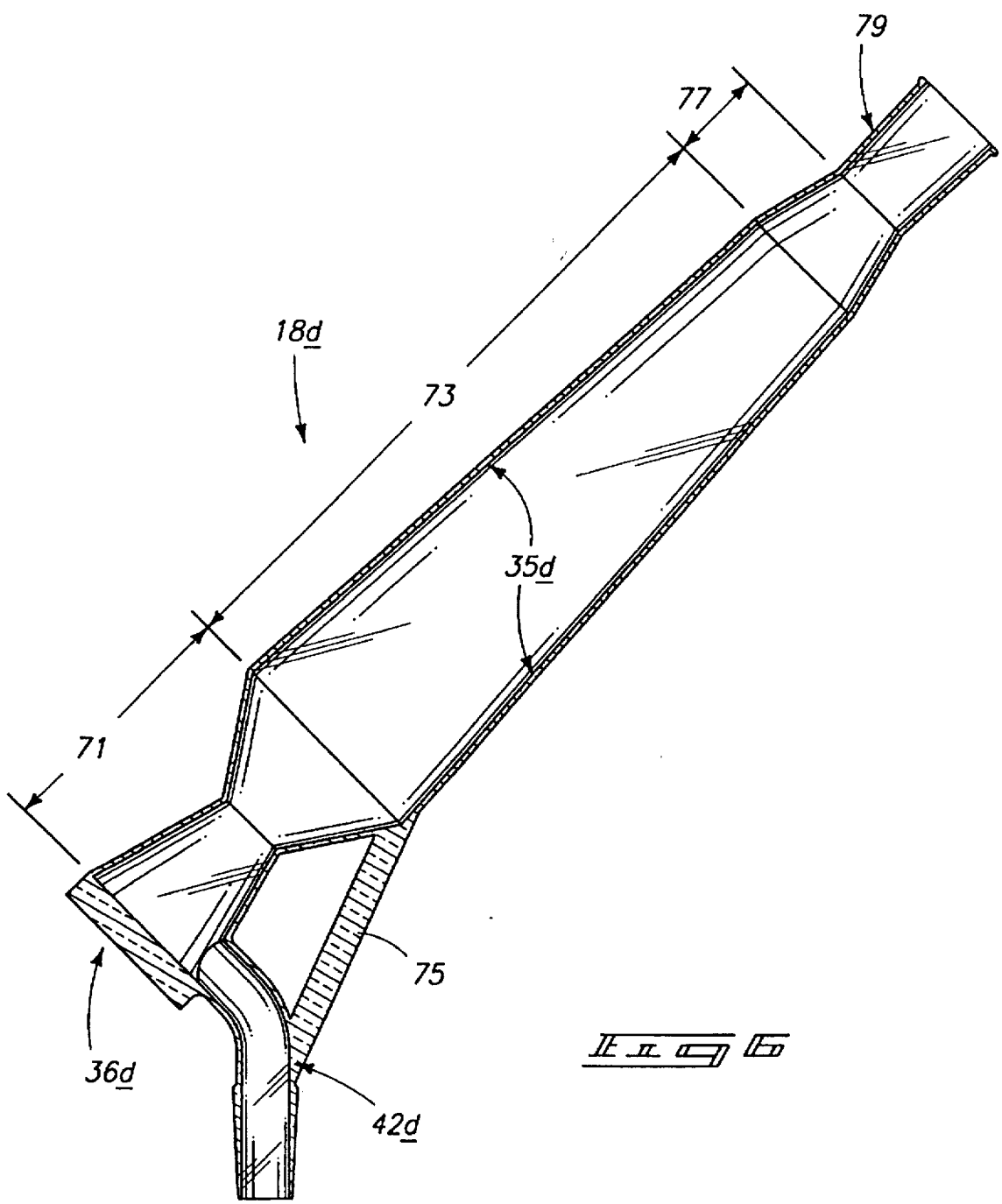
FIG. 6 is a diagrammatic sectional view of another alternate embodiment liquid/vapor separation apparatus in accordance with the invention.
Figure 7:
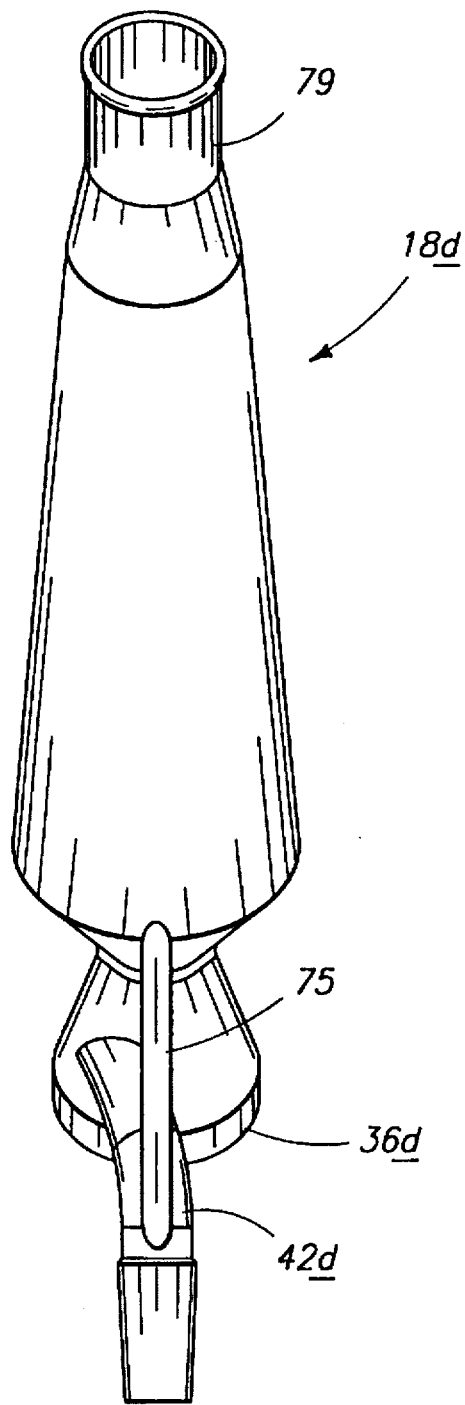
FIG. 7 is a side elevational view of the FIG. 6 apparatus taken at 90° relative to the FIG. 6 view.

An example apparatus in accordance with the invention capable of carrying out the above-described method is shown and described with reference to FIG. 5. Such comprises boiling chamber 16 and separation tube 18c having an associated ultrasonic transducer 46 to induce ultrasonic waves within separation tube 18c. More specifically, ultrasonic transducer 46 is mounted adjacent inlet end region 36c essentially longitudinally behind passageway 42c. The effect will be to induce ultrasonic waves longitudinally along and within elongated body 34c. Alternately and by way of example only, transducer 46 might be configured and/or mounted elsewhere along tubular body 34c to pass ultrasonic waves laterally across the hollowed portion of the tube. In this configuration, multiple transducers would most preferably be utilized. In reduction to practice tests involving ultrasonic power, it was determined that extreme high intensity ultrasonic power did not provide an improving effect, whereas more moderate powers did provide an improved effect. Specifically, 60 volts of ultrasonic power provided a noticeable improvement whereas 90 volts of ultrasonic power did not. One theory for this observation is that the ultrasound at higher powers disrupts the micro droplets as they exit into the separation chamber, thus possibly causing a phase shift of such droplets into the vapor phase. An alternate and more probable theory is that the higher intensities heated the internal sidewalls sufficiently to re-evaporate the condensate.

Where ultrasonic waves are generated longitudinally along the length of an elongated tube body 34, the wave front generated will be other than conformal to the internal side shape of the tube. The generated wave front will typically taper inward a given distance and then radially expand outward. It may be desirable to provide at least a portion of internal sidewalls 35 to have a shape corresponding to that of the ultrasonic or other acoustic wave form to facilitate acoustic wave exposure and corresponding separation of analyte from solvent. FIGS. 6 and 7 illustrate such an alternate embodiment separation tube 18d having internal sidewalls 35d which are other than straight along the length of the apparatus. Specifically, internal sidewalls 35d have a section 71 which corresponds in longitudinal shape to a longitudinally traveling ultrasonic wave emanating from inlet region 36d along expanse 71. This configuration will increase acoustic intensity by a large factor, and thus desirably increase vorticity in the flow.

Walls 35d then taper inwardly along expanse 73 to facilitate gas flow restriction and turbulence. This inward taper will assist in keeping the acoustic pressure relatively constant in this region by compressing the acoustic field to overcome absorption in the vapor. The most desirable conditions in this region are thought to be the induction of standing or traveling vortices through an acoustic streaming mechanism, with the vortices each occupying approximately the full diameter of region 73. Walls 35d then further inwardly taper along an expanse 77 before a chamber outlet 79. The tapering along expanse 77 per chamber length is greater in degree than the tapering in expanse 73. This tapering, combined with the tapering along expanse 73, is intended to intercept droplets propelled by the acoustic waves.

The bent nature of passageway 42d also facilitates turbulence. Further, passageway 42d connects with the main portion of the chamber at an off-center location relative to the longitudinal chamber axis (FIG. 7). This causes the flow to enter the main chamber more tangentially, thus desirably causing the flow to swirl internally around the chamber as it starts to progress along the internal sidewalls. This also facilitates turbulence. A support extension 75 extends between passageway 42d and the body of separator 18d.

The preferred design of the separation chamber will cause the rising vapors repeatedly to contact cooler sidewalls through a number of coordinated mechanisms, such as those described above. Vapor flow conditions are preferably adjusted to minimize laminar flow near the wall, induce boundary-layer shear in that region, and maximize turbulent flow. Conditions impacting such flow include dimensions of the chamber, longitudinal shape of the chamber (e.g., constriction and expansion of the chamber), and flow head (e.g., the vacuum utilized, which partially controls flow velocity).

Further, turbulence vorticity, and directed flow of droplets in the flow are preferably optimized or enhanced by the acoustic waves. The basic dimensions of the chamber to achieve these effects are a function of the acoustic wavelength and the ratio of wavelength to diameter, as modified by the inherent considerations of convective flow as noted. By choosing the appropriate wavelength or frequency of sound, one may size the chamber to accommodate a wide variety of boiling rates and/or restrictions on physical size of the chamber.

At the time of filing this document, the FIGS. 6 and 7 embodiment is believed to be best-mode, or most preferred. Such does, however, show the acoustic interface at region 36d to be flat. It may be possible to increase the effective acoustic or ultrasonic intensity within the chamber by shaping the glass in that region in the form of an acoustic impedance matching horn.

The discussion proceeds with reference to FIG. 8. There schematically illustrated is an enlarged view of liquid test sample withdrawal apparatus 14 (FIG. 1) for withdrawing a liquid test sample from a test sample container and also for cleaning the test sample container from which the sample is withdrawn. Such comprises a longitudinally elongated body 50 having a liquid sample intake end 52. A sample withdrawal passageway is formed within the elongated body, and communicates with the intake end. In the illustrated embodiment, the sample withdrawal passageway is in the form of a centrally oriented tube 54. A cleaning fluid passageway is formed within the elongated body and communicates between a cleaning fluid source and the liquid sample intake end to emit cleaning fluid from the sample intake end. As shown, a cleaning fluid passageway 56 is annularly formed around sample withdrawal passageway 54 within elongated body 50. An upper enlarged body head 58 connects with elongated body 50 and includes a central cavity 60 through which sample withdrawal tube 54 centrally extends. Thus, cavity 60 forms an annular cavity about tube 54, thus communicating with annular cleaning fluid passageway 56. A tube 62 connects with cavity 60 of upper head 58, and connects with a cleaning fluid source.

Liquid sample intake end 52 is comprised of a lower enlarged body head 64. Sample withdrawal tube 54 extends entirely through enlarged lower head 64 to define a sample inlet opening 66. A plurality of lateral openings 68 are provided in enlarged head 64 and communicate centrally and annularly about sample withdrawal tube 54, and communicate with annular cleaning fluid passageway 56. Thus, the cleaning fluid outlet openings 68 are positioned elevationally above the sample inlet opening. Means are provide for raising and lowering elongated body 50 relative to a test sample container 10 (FIG. 1). Example means for raising and lowering elongated body 50 include fluidics, such as pneumatic or hydraulic actuation, or electric or other means for providing an on-demand raising and lowering effect.

An example and preferred construction comprises a fluidically powered liquid test sample withdrawal apparatus, such as is schematically shown in FIG. 8. A fluidic cylinder 70 is formed about elongated body 50. An integral disk-like member 72 is formed centrally about elongated body 50 between upper and lower enlarged body heads 58 and 64. Elongated body 50 is provided to be elevationally movable, thus constituting a movable piston rod. Disk 72 constitutes a piston positioned within fluidic cylinder 70 and associated with piston rod 50 to enable selective raising and lowering of piston rod 50 intake end 52 relative to test sample container 10 (FIG. 1). In the illustrated and preferred embodiment, piston 72 is formed annularly around piston rod 50. Pneumatic or hydraulic lines 74 and 76 connect with fluidic cylinder 70 on opposing sides of piston 72. Such are controlled to enable selective raising and lowering of elongated body/piston rod 50 relative to fluidic cylinder 70 such that the position of head 64 can be positioned in any desired location within the range of movement provided by fluidic cylinder 70.

The discussion proceeds with reference back to FIG. 1 in the utilization of the above-described apparatus and methods. Samples to be concentrated can be introduced to the illustrated system either through sample intake beaker 10 or through a direct sample inline 80. In either event, liquid sample will ultimately pass through manifold A, outwardly through line 82 and into separation tube 18 for collection in the base of boiling chamber 16. The driving force for drawing fluid into boiling chamber 16 would be the creation of vacuum pressure within separation tube and boiling chamber 16. Such would be created by vacuum pump 83, with the vacuum pressure within elongated tube 18 and boiling chamber 16 being controlled via vacuum control valve N-. The discussion proceeds with utilization of fluid extractor/cleaner 14 for withdrawal of sample fluid from sample intake beaker 10. Appropriate sensors would detect the presence of a beaker 10 as well as its vertical extent. Piston rod 50 would then be lowered to the base of beaker 10 for withdrawal of sample to be concentrated therefrom. The preferred manner for raising and lowering piston cylinder 50 is by pneumatics, using illustrated pneumatic valves P2 and P3. Such can be provided with instrument air or some other gas source. In the illustrated embodiment, a nitrogen gas source labeled $N_2$ feeds regulator valves R2 and R3. R3 is a pneumatic control valve for pneumatic cylinder air, while R2 regulates nitrogen gas which is exposed to the sample for $N_2$ blow-down, for creating nucleation sites during the boiling process, and line purge and clean, as will become more apparent from the continuing discussion.

Driving pneumatics for the air cylinder associated with extractor 14 via valves P2 and P3 are provided from $R_3$ through a line 84. R3, P2 and P3 would be energized to lower piston cylinder 50 to position head 64 at the base of beaker 10 for withdrawal of liquid therefrom. A vacuum would be created in boiling chamber 16 and 18 through valve N- with pump 83. Valve AC would be opened which would communicate vacuum withdrawing force to head 64 via lines 82 and 54. A sensor positioned in line 82 would detect gas flow, thus signifying completion of sample withdrawal from beaker 10 and lines 54 and 82.

Valve AC would then be closed and heaters associated with boiling chamber 16 activated. Vacuum pressure would then be readjusted, as necessary or desired. Immediately prior to and during boiling, nitrogen gas would be provided (to create nucleation sites) through valve R2 via line 86, through flow meter 88, line 90 and open valve BA.

Precious sample is also anticipated to remain on the sidewalls of inlet beaker 10. Accordingly, means are provided for washing down the internal sidewalls of beaker 10 with solvent, and transferring such solvent to separation tube 18 and boiling chamber 16 for concentration prior to fluid transfer to transfer module 22. A line 108 connects with line 100, and includes an in-line solvent control valve F-. Line 62 extends from line 108 to annularly feed spray cleaning solvent through elongated piston rod 50 and outwardly of head 64, as is structurally described with reference to FIG.

8 above. A line 110 extends from line 108 and terminates immediately adjacent the lower external portion of piston rod 50 for spraying cleaning solvent thereon for cleaning of piston rod 50. Liquid collecting in beaker 10 would then be withdrawn by vacuum pressure into evaporation tube 18 and boiling chamber 16.

Specifically and preferably, cylinder 50 and head 64 are positioned at a percentage of beaker 10 height (80%) and the rinse solvent is started by opening valves P1 and MP. After a given time the rinse head 64 and cylinder 50 are lowered to a second rinse position, that is again a percentage of beaker height (40%). The total rinse is determined by time, with a percentage of total time given at each position. Once the rinse time has expired, Valves P1 and F- are closed and head 64 is lowered to the bottom of beaker 10. The rinse is then transferred to the boiling chamber 16 in the same manner as described above. The number of rinse cycles is user selectable.

Boiling in the above-described manner continues until the volume of the sample is reduced to level L1 in lower collection tube 90. Rising solvent vapor flows through vacuum pump 83 to some solvent recycler system 85. Protocol will typically require that L1 be reached within a certain period of time. Where L1 is not reached, the sample would be considered viscous (non-reducing) and desired to be purged from the system. To purge such a sample that does not satisfactorily concentrate to level L1, such would be discarded through valve BB, through line 91 and into a difficult sample beaker 92. During such purging of the sample, valves N- and BA would be closed and valve AD would be open to provide purging $N_2$ nitrogen gas flow and driving force to expel all of the sample into beaker 92.

Assuming the sample boiled down to level L1 in tube 20 within a sufficient time period, boiling would continue to further concentrate the sample to level L2. Protocol would also typically require that tome period from boiling from level L1 to L2 occur within a certain period of time. If the level L2 is not reached within the required period, the remaining sample would be purged into beaker 92 in a manner described above. However if level L2 is reached within the prescribed time limit, fluid passage to transfer module 22 occurs. The driving force for such transfer is accomplished with $N_2$ gas by pressurizing boiling chamber 16 through valve AD. During such transfer, valve BC, valve CC, valve DB, and valve LP are open. Fluid flows through a line 112 to transfer module 22. Outlet from valve LP feeds a line 97 to provide venting to a gas/liquid waste collection reservoir 85.

Transfer module 22 also has associated level indicators L1 and L2. Level L1 in transfer module 22 is selected such that complete transfer of fluid from boiling chamber 16 at a level below tube 20 L2 will be below transfer module 22 level L1.

Once initial transfer has been completed in the above-described manner to transfer module 22, additional sample is extracted from evaporator 18 and boiling chamber 16. During initial concentration in chamber 16 and tube 18, sample will splatter onto the associated sidewalls. In order to collect such splattered sample, rinses and subsequent concentration by additional boiling is conducted. Such occurs through a pressurized solvent rinse system, which includes a solvent reservoir 96. A pneumatic valve control line 98 extends from regulator valve R3 to a pressure control valve P1. Valve P1 is utilized to control opening and closing of a solvent outlet flow valve MP. A solvent outlet line 100 flows from solvent reservoir 96 to valve AB. Solvent reservoir 96 is pressurized from nitrogen source $N_2$ via a line 102. A regulator valve R2 provides $N_2$ to line 102 for providing and controlling pressure within pressurized solvent reservoir 96. A safety relief valve RV1 is associated with solvent reservoir 96.

To transfer rinsing solvent to elongated tube 18 and boiling chamber 16, P1 would be activated to open solvent flow valve MP. Solvent would then flow through line 100 through open valve AB, through line 82, and into separation tube 18 and boiling chamber 16. With a sufficient volume of solvent injected into separation tube 18 and boiling chamber 16. After the solvent is injected into boiling chamber 16, the internal pressure is increased to a positive pressure (5 psig), selectable by the operator. This action raises the boiling point of the liquid. The heaters are turned on and the liquid is allowed to heat to a set point just below the liquid's boiling point. When the set point (as indicated by a thermocouple) is reached, a vacuum (-5 psig) is pulled on the boiling chamber, and $N_2$ is introduced through valve BA. The lower pressure reduces the boiling point of the liquid below the actual boiling point, creating a super-heated fluid. The introduction of the $N_2$ creates a nucleation site for the super-heated fluid, and it immediately erupts into rapid boiling (This phenomenon in the chemistry art is referred to as "bump" or "bumping", and is undesirable in the general chemistry art. It is however purposefully utilized in accordance with this aspect of the invention). The sudden rapid boiling blows solvents from the boiling chamber 16 into the separation chamber 18, thus rinsing the inside walls of both the boiling chamber and separation chamber. Solvent vapors would be ejected from separation tube 18 through valve N- and outwardly into solvent recycler 85.

After bumping, any further sample and solvent would then collect and concentrate within the lower portion of lower collection tube 20, and be transferred to transfer module 22 in a manner described above. Multiple rinses might be conducted in the above manner, as selected by the operator, until no further sample collects at the base of lower collection tube 20. Even with all the subsequent rinsing and collection of sample from separation tube 18 and boiling chamber 16, the total volume of the collected sample in transfer module 22 will be such that the volume is below level L1 in transfer module 22. If more rises are requested by the operator than can be handled by the transfer module 22 at level 1, the remaining rinses will be rerouted to waste reservoir 95.

Analysis protocol will typically require that sample of a given volume be provided for the next step in analysis external of the system illustrated by FIG. 1. For example, it is anticipated that a sample concentrated to 10 milliliters will be desired for subsequent analysis. Accordingly, a level L2 would correspond to approximately 10 milliliters, with a requirement then that the sample be brought up to level L2 prior to further processing. In accordance with the above-described preferred method, solvent would be added to transfer module 22 by opening valves MP, CB, DB, and LP. Solvent would be allowed to flow through such valves and associated tubing until the sample volume within transfer module 22 was brought to level L1. At this point, any bubbles or turbulence caused by bringing the level to L1 are allowed to settle. Solvent is then added such that a precise level L2 within transfer module 22 can be reached. Valve CB is fed via a line 106 which connects with line 100 for providing solvent source. The final volume in transfer chamber 22 located at sensor L2 is calibrated to include the volume of liquid remaining in line 112 and the line interconnecting manifolds C and D.

Once collection and any concentration in transfer module 22 is complete, the next goal is to get the sample therefrom into sample vial 12 for removal from the system. Such is accomplished by opening valves DB, CA and H-. Outlet from valve CA flows via a line 114 to valve H- which is capable of directing fluid directly out of the system bypassing sample collection valve 12 via a line 116, or to collection vial 12 via a line 118. During such transfer to sample vial 12, valve EA would be open to vent via line 120 to line 94, and correspondingly waste reservoir 95. Liquid sample of the desired volume would collect within sample vial 12. A pressurized $N_2$ gas driving force for transferring the liquid to sample vial 12 would be provided via a line 122, which connects with $N_2$ line 86, to a control valve GB and ultimately into transfer module 22. A sensor in line 114 will determine when all the sample has been ejected from transfer module 22.

Sample in nitrogen gas feed line 118 feeds into a container cap block 124 which is sized in one instance to mate with the top of sample vial 12, and in another instance with a lower cap supporting base 126. Lower supporting base 126 is raised and lowered via a double-acting air cylinder 128. Line 130 joins with $N_2$ source line 84. With a sample vial 12 supported by base 126, pneumatic force from line 130 can be utilized to raise or lower the cylinder to enable insertion and removal of vial 12 from the apparatus. Where no vial 12 is supported by base 126, pneumatic force will position base 126 upwardly against cap block 124 creating a fluid seal therebetween.

With transfer module 22 being completely emptied to fill sample vial 12, the fluid seal is released, and sample vial 12 removed and subjected to any desired subsequent processing. Then for cleaning purposes, the operator has the option of doing a complete system wash, or washing individual sections. The washing of individual sections is a preferably a subset of a computer-controlled overall wash process. Discussion of a preferred sequenced complete process follows. If sections are washed individually in a manual mode, the following sequence would of course not necessarily be followed The first system washed is boiling chamber 16 and separation chamber 19. Vacuum drawing pressure is established in the boiling chamber, and then valves MP and AB are opened allowing clean liquid to flow from reservoir 96 for some predetermined time period. Once the flow is complete, the boiling chamber pressure is set to a selected positive value (i.e., 5 psig) by setting vacuum valve N- and opening AD. The solvent is then allowed to heat and "bump" as described above during the rinse cycle. After bumping, the liquid is allowed to drain out of the separation chamber 18 into the boiling chamber 16. After the preset drain time has expired, the liquid is transferred to waste by opening valves BC, CC and DA and pressurizing the boiling chamber with $N_2$. A sensor in line 114 determines when the transfer is complete.

The next section washed is transfer chamber 22. Vent valve LP is opened, and valve GA is opened for a given time period allowing cleaning liquid to flow into the transfer chamber. At the end of liquid addition, valves LP and GA are closed and valves DB and DA are opened. Transfer chamber 22 is then pressurized by opening valve GB, thus forcing the liquid to travel through line 112 to 94 and out to waste at 95. A sensor in line 112 determines when the transfer is complete. To insure no wash was trapped in manifold D and the line extending between manifolds C and D, CB then CD, respectively, are momentarily opened and closed to allow clean liquid (then $N_2$) to flow through the C and D manifolds, and out line 94.

The final wash is to clean output chamber parts 124 and 126. With the vial 12 removed, pneumatic pressure from line 130 is used to move base 126 into contact with head 124, using cylinder 128, thus creating a seal between the two halves. Valves MP, CB, CA, and EB are opened (H- by default allows flow into the output chamber) allowing pressurized fluid container 96 to flow through the closed 124 and 126 output chamber halves. After a timed fluid flow is completed, $N_2$ is introduced to dry the lines and output chamber. Valves CA, EB remain open and valve CD is opened and closed in a timed sequence to slowly build the pressure in the closed 124 and 126 halves. This timed sequence prevents an in-rush of $N_2$ pressure that can override the pneumatic force generated by cylinder 128, and allow cleaning liquid to escape the seal. The time sequences starts out with a short timed burst of $N_2$ (opening valve CD), followed by a delay with the valve CD closed. The total time burst is then increased by the original amount of time, and the delay decreased by the same original time value. This sequence is repeated until the delay time has decreased to zero, with $N_2$ remaining on. After another time period used to finalize the drying of lines and output chamber halves 124 and 126, valves CD, CA, and EB are closed. Liquid and $N_2$ flow out of line 120 to line 94 to waste reservoir 95.

An alternate $N_2$ blow-down concentration within transfer module 22 might also be desirably conducted prior to any transfer of sample to outlet vial 12 as will now be described. If the closed output heads 124 and 126 are at a position that sensors determine a 1.5 mL vial (with adapter to fit head 126) as opposed to a 10 mL vial, the instrument directs an $N_2$ blow-down process. With sample having been concentrated from boiling chamber 16 and separation tube 18 and having been transferred into transfer module 22 with a level below L1, valves CD and DB are opened to bubble nitrogen gas through the sample. When three-way valve J- is switched, $N_2$ is routed through needle valve KN that controls the flow of gas into the sample. Valve GB is also opened to allow $N_2$ to flow into transfer chamber 22 above the sample level. Valve LP is opened to vent the gases and evaporating liquid. The system can also be configured to just bubble-up through the liquid or blow on top of the liquid.

In order to sense the end point of the $N_2$ blow-down process, transfer chamber 22 has a reduced (smaller diameter) section that holds a small amount of liquid (approx. 2 mL). A sensor $L_o$ is placed on this reduced section. The gases flow through the sample for a predetermined time (i.e., 20 sec.), then the gas is turned off and the liquid allow to settle (i.e., 2 sec.). The sensor is checked to determine if liquid is still present. When liquid is present, the process is repeated until no liquid is detected. At that point additional solvent is added in very small quantities. This liquid addition is accomplished by turning on valves LP and DB.

Next, valve CB is quickly (timed action) opened and closed, followed by CD quickly (timed action) being opened and closed. CD ($N_2$ gas) is opened long enough to push the liquid introduced into the lines by valve action CB into the transfer chamber. The liquid is allowed to settle, and then the sensor is read. The liquid addition is repeated until the sensor again sees the liquid and ends the process. Nitrogen blow-down in this manner can serve to further concentrate sample with transfer module 22 to a level below the level at which the liquid volume occurred via transfer from boiling chamber 16.

In the course of such nitrogen blow-down concentration, sample might undesirably bubble upwardly and adhere to the internal sidewalls of transfer module 22. To facilitate removal of the sample from these walls, the internal walls of transfer module 22 could be cleaned by closing valve GB and subsequently opening valve GA to spray solvent into transfer module 22. Such cleaning and nitrogen bubbling would continue until some solvent level below the illustrated Level L0 in transfer module occurred, and then would be raised back up to L0 as discussed by alternating valves CA and CD. Then, the remaining sample would be transferred to outlet vial 12 or directly through outlet line 116, in a manner described above.

While operating this instrument, the operator may want to use the $N_2$ blow-down feature without using boiling chamber 16 and separation chamber 18. This can be accomplished in a manual operation mode. To get the sample into transfer chamber 22, valve GB would be turned on and three-way valve K- switched. Vacuum pump 83 would be turned on and a suitable drawing pressure (i.e., −3 psi) would be set on vacuum control valve N-. After a suitable time, the user would turn on the liquid flow. This is done by holding the contained sample and inserting a tube 99 into the sample. The operator verifies that the sample is ready, and then valves DC and DB are opened. Liquid flows through line 112 and into the transfer chamber 22. A sensor on line 112 signals when the transfer is complete. The operator can then repeat this step if desired. If L1 sensor in transfer chamber 22 detects liquid during the transfer, the process is halted and the operator is informed transfer chamber 22 is full. At that point the $N_2$ blow-down process can proceed as described above.

In compliance with the statute, the invention has been described in language more or less specific as to structural, compositional and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of processing a test sample to separate an analyte in the sample from a solvent in the sample, the analyte having a higher boiling temperature than the solvent, the method comprising the following steps:

boiling the test sample containing the analyte and solvent in a boiling chamber to a temperature greater than or equal to the solvent boiling temperature and less than the analyte boiling temperature to form a rising sample vapor mixture, the sample vapor mixture comprising vaporized solvent and liquid analyte physically transported therewith;

passing the sample vapor mixture from the boiling chamber to an elongated primary separation tube, the primary separation tube having internal sidewalls and a longitudinal axis, the longitudinal axis being angled between vertical and horizontal and thus having an upper region and a lower region;

passing a turbulence inducing wave into the separation tube to enhance separation of physically transported analyte from the vaporize solvent;

collecting the physically transported liquid analyte on the internal sidewalls of the separation tube; and flowing the collected analyte along the angled internal sidewalls of the separation tube to and past the separation tube lower region.

2. The method of processing a test sample of claim 1 further comprising cooling the separation tube sidewalls to a temperature below the solvent boiling temperature.

3. The method of processing a test sample of claim 1 wherein the lower region of the separation tube is elevationally higher than the boiling chamber and connected therewith, the method further comprising:

bumping liquid analyte and solvent present in the boiling chamber to cause such liquid to be blown into the separation tube to rinse inner walls of the separation tube and boiling chamber.

4. The method of processing a test sample of claim 1 wherein the lower region of the separation tube is elevationally higher than the boiling chamber and connected therewith, the step of flowing the collected analyte comprising passing the analyte from the separation tube lower region back into the boiling chamber by gravity.

5. The method of processing a test sample of claim 1 wherein the separation tube and boiling chamber are connected to one another via a passageway, the passageway including a bend, the passing step thereby occurring along a path between the boiling chamber and elongated primary separation tube which includes a bend.

6. The method of processing a test sample of claim 1 wherein the lower region of the separation tube and boiling chamber are connected to one another via a passageway, the passageway including a bend and being void of horizontal sections, the lower region of the separation tube and the passageway being elevationally higher than the boiling chamber, the step of flowing the collected analyte comprising passing the analyte from the separation tube lower region through the passageway and back into the boiling chamber by gravity.

7. The method of processing a test sample of claim 1 wherein the turbulence inducing wave comprises an acoustic wave.

8. The method of processing a test sample of claim 1 wherein the turbulence inducing wave comprises a sonic wave.

9. The method of processing a test sample of claim 1 wherein the turbulence inducing wave comprises an ultrasonic wave.

10. The method of processing a test sample of claim 1 wherein the turbulence inducing wave comprises pulsing vacuum pressure within the separation tube.

11. The method of processing a test sample of claim 1 wherein the turbulence inducing wave is generated by pulsing a gas through the separation tube.

12. The method of processing a test sample of claim 1 further comprising passing a turbulence inducing wave into the separation tube to enhance separation of physically transported analyte from the vaporized solvent; and wherein the lower region of the separation tube is elevationally higher than the boiling chamber and connected therewith, the step of flowing the collected analyte comprising passing the analyte from the separation tube lower region back into the boiling chamber by gravity.

13. The method of processing a test sample of claim 1 wherein the lower region of the separation tube and boiling chamber are connected to one another via a passageway, the passageway being other than straight and void of horizontal sections, the lower region of the separation tube and the passageway being elevationally higher than the boiling chamber, the step of flowing the collected analyte comprising passing the analyte from the separation tube lower region through the passageway and back into the boiling chamber all by gravity; and the method further comprising passing a turbulence inducing wave into the separation tube to enhance separation of physically transported analyte from the vaporized solvent.

* * * * *